United States Patent [19]
Grim et al.

[11] Patent Number: 5,823,981
[45] Date of Patent: Oct. 20, 1998

[54] RESILIENT ORTHOPAEDIC SUPPORT WITH INDEPENDENTLY STRETCHABLE LAYERS

[75] Inventors: Tracy E. Grim, Broken Arrow, Okla.; Alec D. Bobroff, Saratoga, Calif.; John Morgan Bourne, Redondo Beach, Calif.; Joseph Michael Iglesias, Agoura, Calif.

[73] Assignee: Royce Medical Company, Camarillo, Calif.

[21] Appl. No.: 254,111

[22] Filed: Jun. 6, 1994

[51] Int. Cl.$^6$ ........................................................ A61F 5/00
[52] U.S. Cl. ................................. 602/26; 602/13; 602/20; 602/63
[58] Field of Search ................................. 602/5, 13, 23, 602/20, 26, 61–63; 607/112

[56] References Cited

U.S. PATENT DOCUMENTS

| | | | |
|---|---|---|---|
| 3,375,821 | 4/1968 | Meek | 602/26 |
| 3,901,225 | 8/1975 | Sconce | 602/13 |
| 3,934,583 | 1/1976 | Hollingshead et al. | 602/62 |
| 4,116,236 | 9/1978 | Albert . | |
| 4,250,578 | 2/1981 | Barlow | 602/26 X |
| 4,445,505 | 5/1984 | Labour et al. . | |
| 4,474,573 | 10/1984 | Detty . | |
| 4,492,227 | 1/1985 | Senn et al. | 602/26 X |
| 4,509,750 | 4/1985 | Last | 607/112 X |
| 4,651,722 | 3/1987 | Karczewski . | |
| 4,832,010 | 5/1989 | Lerman . | |
| 4,870,956 | 10/1989 | Fatool et al. . | |
| 4,887,590 | 12/1989 | Logue et al. . | |
| 4,938,207 | 7/1990 | Vargo . | |
| 4,961,418 | 10/1990 | McLaurin-Smith . | |
| 4,986,263 | 1/1991 | Dickerson et al. . | |
| 5,139,477 | 8/1992 | Peters . | |
| 5,154,690 | 10/1992 | Shiono . | |
| 5,263,923 | 11/1993 | Fujimoto | 602/62 |
| 5,407,421 | 4/1995 | Goldsmith | 602/26 X |
| 5,451,201 | 9/1995 | Prengler | 602/13 X |

*Primary Examiner*—Linda C. Dvorak
*Attorney, Agent, or Firm*—Oppenheimer Poms Smith

[57] ABSTRACT

An orthopaedic support having outer and inner resilient layers wherein the outer resilient layer is comprised of neoprene or another material suitable for surrounding and supporting a portion of the human anatomy through compression and a inner resilient layer generally coextensive with a substantial portion of the outer resilient layer which may be comprised of a material selected to enhance the performance and comfort of the orthopaedic support. The inner and outer resilient layers may be secured together in discrete zones but are otherwise freely stretchable or movable relative to one another. Where desired, the outer resilient layer may be provided with an aperture configured to receive a discrete area of the supported body member such as the knee cap which may be sensitive to pressure. The inner resilient layer of such a support may be provided with a corresponding aperture or, in the alternative, the inner resilient layer may extend across the aperture in the outer resilient layer. In the latter case, it may be advantageous if the inner resilient layer is comprised of material suitable for exerting a light restraining force on the sensitive area. A supplemental resilient member may be provided adjacent the inner surface of the outer resilient layer or the outer surface of the inner resilient layer after which the overlapping portions may be subjected to heat and compression so as to decrease the thickness (and increase the density) of discrete portions of the supplemental resilient member and the overlapping portion of the inner or outer resilient layer and to cause the uncompressed or partially compressed portions of such member and layer to form an interface whereby the non-adjoining surface of the supplemental resilient member is substantially flush with the portion of the surface of the inner or outer resilient layer adjacent thereto.

27 Claims, 3 Drawing Sheets

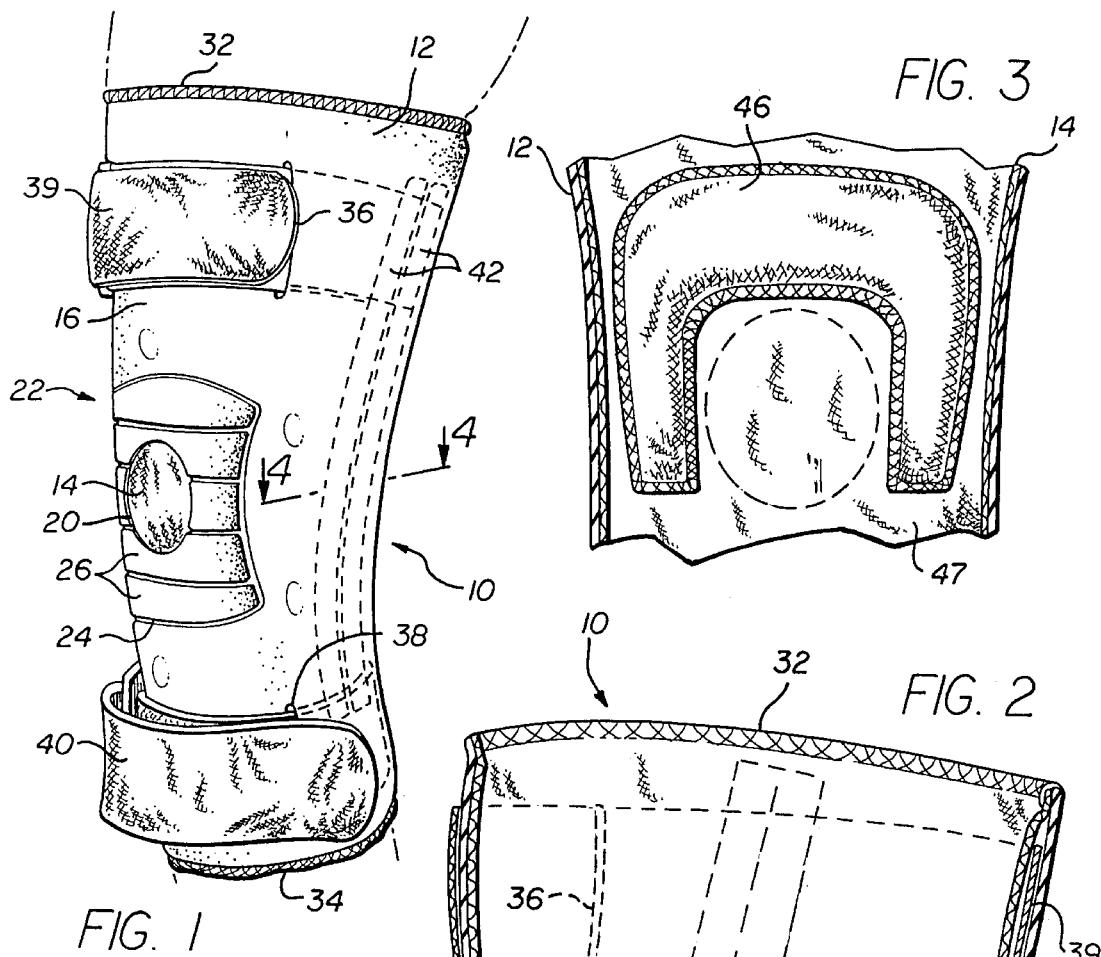
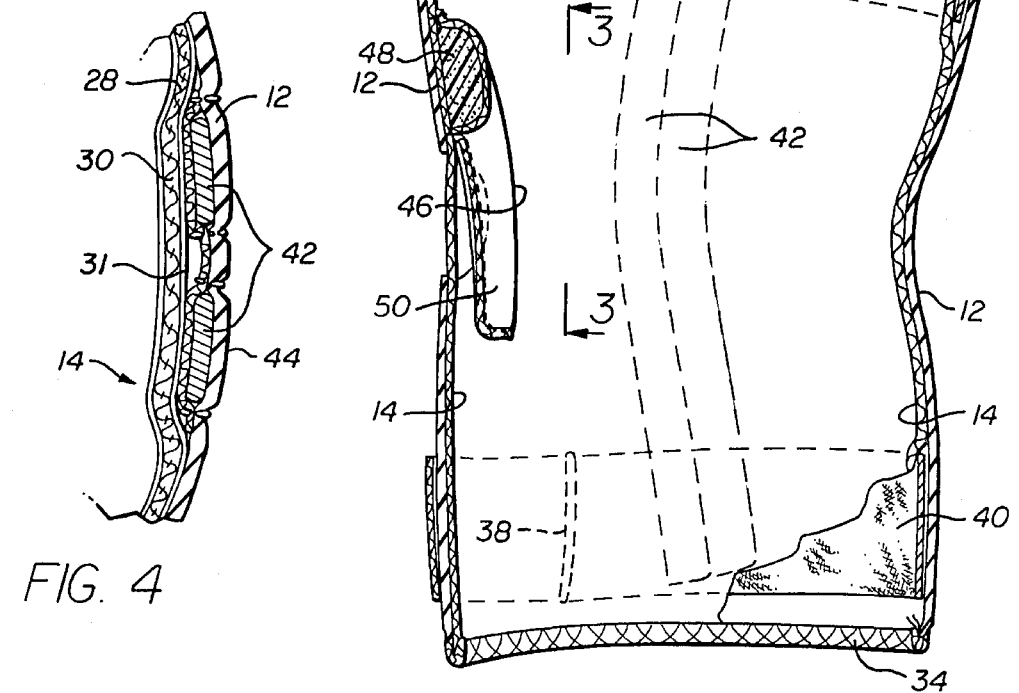

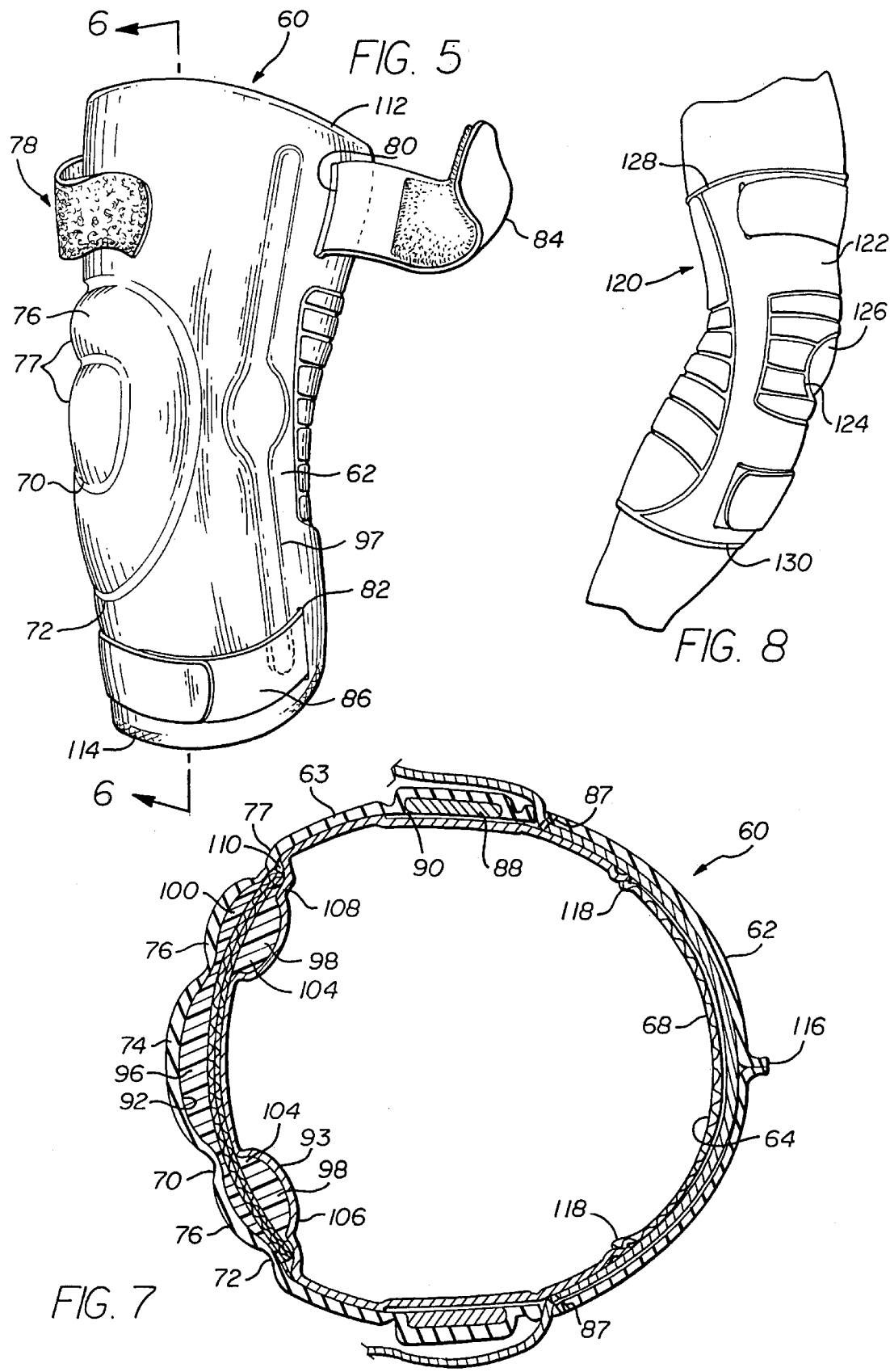

RESILIENT ORTHOPAEDIC SUPPORT WITH INDEPENDENTLY STRETCHABLE LAYERS

BACKGROUND OF THE INVENTION

Related Patent Applications

The present invention is related to the orthopaedic support disclosed and claimed in U.S. patent application Ser. No. 08/018,004, filed on Feb. 16, 1993, entitled "Formed Resilient Orthopaedic Support", which issued as U.S. Pat. No. 5,334,135 on Aug. 2, 1994 and which is assigned to the assignee of the present invention.

1. Field of Invention

The present invention relates generally to orthopaedic supports for the human anatomy and, more particularly to orthopaedic supports adapted for use in surrounding and supporting a human body member through compression.

2. Description of Related Art

Various orthopaedic supports have been developed to stabilize and protect injured or strained parts of the human anatomy such as knees, ankles and elbows. Many of these supports are made from flexible resilient materials which, when stretched over a knee or other body part, provide support to the underlying body part through compression.

Resilient orthopaedic supports are typically composed of neoprene rubber or similar closed cell elastomers. The elasticity and relatively high density of such materials generally translates into the desired compressive support. Many of the available resilient supports also include additional material layers which are bonded to or otherwise adhere to the selected elastomer. Such supports are disclosed in U.S. Pat. No. 4,474,573 issued to Detty and U.S. Pat. No. 4,651,722 issued to Karczewski.

A number of problems arise with these orthopaedic supports. A first problem relates to the thermal non-conductivity of closed cell elastomers. Because the elastomers are generally of low thermal conductivity, the heat which is typically generated between such a support and the underlying body part over which it is stretched is not dissipated. Accordingly, heat tends to accumulate between the skin and the support during prolonged use.

While the application of heat to an injured or strained area during use may alleviate pain and, in some instances, accelerate the healing process, the prolonged application of undissipated heat to an injured area has been known to cause skin irritation and result in abrasions, heat rashes and dermatitis, especially at points of bending such as around the back or popliteal area of the knee.

A second set of problems relates to the perspiration which typically accumulates between these supports and the supported body part and the inability of closed cell materials to absorb or wick such perspiration away from the supported body part. Accumulated perspiration between such supports and the supported body part during prolonged physical activity has been known to exacerbate the skin irritation problems associated with heat accumulation described above.

The accumulation of perspiration between skin and a conventional support may also cause the support to shift or migrate from its preferred location relative to the underlying body part. The migration of an orthopaedic brace during use can result in the aggravation of an unsupported or partially supported body part.

A third type of problem which may arise relates to the tendency of resilient orthopaedic supports to bunch up whenever the supported body part is flexed. This bunching tends to be uncomfortable to the user and may chafe or even bruise the user's skin. Additionally, the edges of the typical support are die-cut, thereby exposing the user's skin to allergenic support materials such as neoprene.

Notably, conventional resilient orthopaedic supports typically provide uniform circumferential compression about the body part over which the support is stretched. The compression applied by such supports can be painful to the user if any portion of supported body member is severely bruised or abraded or if any portion is otherwise sensitive to pressure. For example, a person might suffer from a common ailment of the knee known as chondromalacia. Chondromalacia is a condition of the patellofemural joint which can be extremely painful and possibly disabling if the knee cap or patella engages the underlying thighbone or femur. A person suffering from chondromalacia will probably not be able to wear a conventional resilient knee support because the pressure applied by the support over the knee cap will generate unbearable pain in the patellar region, especially when the injured knee is flexed.

In an attempt to resolve problems associated with the chondromalacia or other painful conditions of the patellar region of the knee which are exaggerated upon application of pressure to the patella, several available orthopaedic braces provide an opening in the patellar region so as to relieve pressure otherwise exerted on the patella. This feature is disclosed in the above mentioned U.S. Pat. Nos. 4,474,573 and 4,651,722 as well as U.S. Pat. No. 5,139,477 issued to Peters.

While such an approach may be acceptable under some circumstances, it is not always preferred, especially for persons engaging in strenuous activities. During such activities, a person's knee may be subjected to relatively strong lateral and rotational forces. These forces can result in subluxation or dislocation of the patella.

The risk of patellar subluxation or dislocation (which, at times, is significantly greater in an injured knee) can be substantially reduced if the orthopaedic support provides at least a light restraining force to the patella. Accordingly, while currently available orthopaedic knee supports may resolve problems associated with conditions such chondromalacia or patellar subluxation, none of the available supports resolve problems encountered by persons having both types of problems.

Additional problems associated with conventional resilient orthopaedic supports relate to supplemental orthopaedic members that may be attached thereto. Supplemental orthopaedic members may include gel packs, inflatable bladders, pumps, straps, and lateral support apparatus such as stays and strut-and-hinge assemblies. Since these items are usually sewn to the outside of a conventional supports and protrude outwardly therefrom, they tend to get caught on other objects thereby causing damage to the support. In some instances, athletes in need of orthopaedic support have been prohibited from wearing such supports during competition because contact with such protruding parts has caused injuries to the user and to other competitors. In such cases, the athletes either forego competing or, in the alternative, compete with increased risk of further damage to the injured body part.

While it would be desirable to provide an orthopaedic support wherein the desired supplemental orthopaedic members are attached to the inside region of such supports, i.e., between the support and the supported body member, the placement of many such supplemental orthopaedic members between the outer resilient member and the user's skin would result in extreme discomfort to the user.

Notably, some of the problems associated with conventional resilient orthopaedic supports were resolved by the orthopaedic support disclosed and claimed by the above-identified inventors in pending U.S. patent application Ser. No. 08/018,004, which application is discussed in greater detail hereinafter and which is incorporated by this reference herein.

However, notwithstanding the features and advantages of each of the resilient orthopaedic supports describe above, there remains a need for an improved resilient orthopaedic support.

SUMMARY OF THE INVENTION

It is therefore a primary object of the present invention to provide a resilient orthopaedic support suitable for use in protecting an injured or strained body part such as the knee wherein the support, when stretched over the injured or strained body part, can support and stabilize the part through compression while simultaneously exerting only a light restraining force on a sensitive area such as the patella.

It is a further object of the present invention to provide such an orthopaedic support with a non-abrasive skin-engaging layer having sufficient porosity to mitigate against the problems associated with prolonged use of such a support.

It is yet an additional object of the present invention to provide such a support with supplemental orthopaedic members which may be disposed between the supported body part and a resilient layer composed of a material suitable for supporting the body part through compression.

It is also an object of the present invention to provide an orthopaedic support having the foregoing features at a low cost.

Generally stated, an orthopaedic support that satisfies the foregoing objects includes a outer resilient layer comprised of neoprene or another material suitable for surrounding and supporting a portion of the human anatomy through compression and an inner resilient layer generally coextensive with a substantial portion of the outer resilient layer which may be comprised of a material selected to enhance the performance and comfort of the orthopaedic support. The inner and outer resilient layers may be secured together in discrete zones but are otherwise freely stretchable or movable relative to one another.

In most cases, it will be preferable if the inner resilient layer includes a non-abrasive porous fabric layer adjacent the supported body part which will protect the underlying skin from irritation which might otherwise occur during use by reason of contact with the outer resilient layer. The skin-protecting fabric layer is preferably without seams in areas of the support which are prone to bunching so as to further reduce the likelihood of skin irritation.

Where desired, the outer resilient layer may be provided with an aperture configured to receive an area of the supported body member such as the knee cap which may be sensitive to pressure. The inner resilient layer of such a support may be provided with a corresponding aperture or, in the alternative, the inner resilient layer may extend across the aperture in the outer resilient layer. In the latter case, it may be advantageous if the inner resilient layer is comprised of a material suitable for exerting a relatively light restraining force on the sensitive area. An orthopaedic support so constructed can generate non-uniform circumferential compression about a supported body part.

In accordance with the present invention, a supplemental resilient member may be provided adjacent the inner surface of the outer resilient layer or the outer surface of the inner resilient layer. Thereafter, the overlapping portions of such member and layer together are subjected to varying amounts of heat and compression using compression molding apparatus. The preferred apparatus is configured to decrease the thickness (and increase the density) of certain corresponding portions of such member and layer and to cause the uncompressed or partially compressed portions of such member and layer to form an interface whereby the non-adjoining surface of the supplemental resilient member is substantially flush with the portion of the adjoining layer which circumscribes the supplemental resilient member.

Advantageously, straps, gel-filled pads, inflatable or pre-inflated bladders, pumps, foam pads, stays, struts, and other supplemental orthopaedic members may be provided between the inner and outer layers of an orthopaedic support in accordance with the present invention without discomfort to the user.

In an alternative embodiment of a resilient orthopaedic support in accordance with the present invention, the resilient orthopaedic support is composed of a first resilient member configured to extend around a portion of the human anatomy and provide support through compression. The first resilient member is provided with an aperture configured to relieve the pressure exerted by the first resilient member from a discrete area of the supported body member. A second resilient member suitable for exerting a light restraining force on the discrete area is attached to the first resilient member so as to extend across the aperture in the first resilient member. This orthopaedic support also generates non-uniform circumferential compression about a supported body part.

A more complete understanding of the present invention will be afforded to those skilled in the art from a consideration of the following detailed description of the preferred exemplary embodiments thereof and to the appended sheets of drawings which will be described briefly hereafter.

BRIEF DESCRIPTION OF THE DRAWING

FIG. 1 is a perspective view of an exemplary embodiment of an orthopaedic knee support in accordance with the present invention.

FIG. 2 is a cross-sectional view of the orthopaedic knee support of FIG. 1 with a cut-out to show a portion of a free running strap disposed between the inner and outer resilient layers;

FIG. 3 is a partial cross-sectional view of the orthopaedic knee support of FIG. 2 taken in the direction indicated by arrows 3—3 in FIG. 2, showing a patella buttress attached to the inner surface of the inner resilient layer of the orthopaedic knee support shown therein;

FIG. 4 is a partial transverse sectional view of the orthopaedic knee support of Fig.1 taken in the direction of arrows 4—4 in FIG. 1, enlarged to show a pair of lateral stays disposed between the inner and an outer layers with the inner resilient layer including an elastomeric layer disposed between two knitted fabric layers.

FIG. 5 is a perspective view of an alternative preferred exemplary embodiment of an orthopaedic knee support in accordance with the present invention.

FIG. 7 is a transverse cross-sectional view of the orthopaedic knee support shown in FIG. 5 taken in the direction indicated by arrows 7—7 in FIG. 6; and FIG. 8 is a preferred exemplary embodiment of an orthopaedic elbow support in accordance with the present invention.

DETAILED DESCRIPTION OF EXEMPLARY PREFERRED EMBODIMENTS

Figure 6:
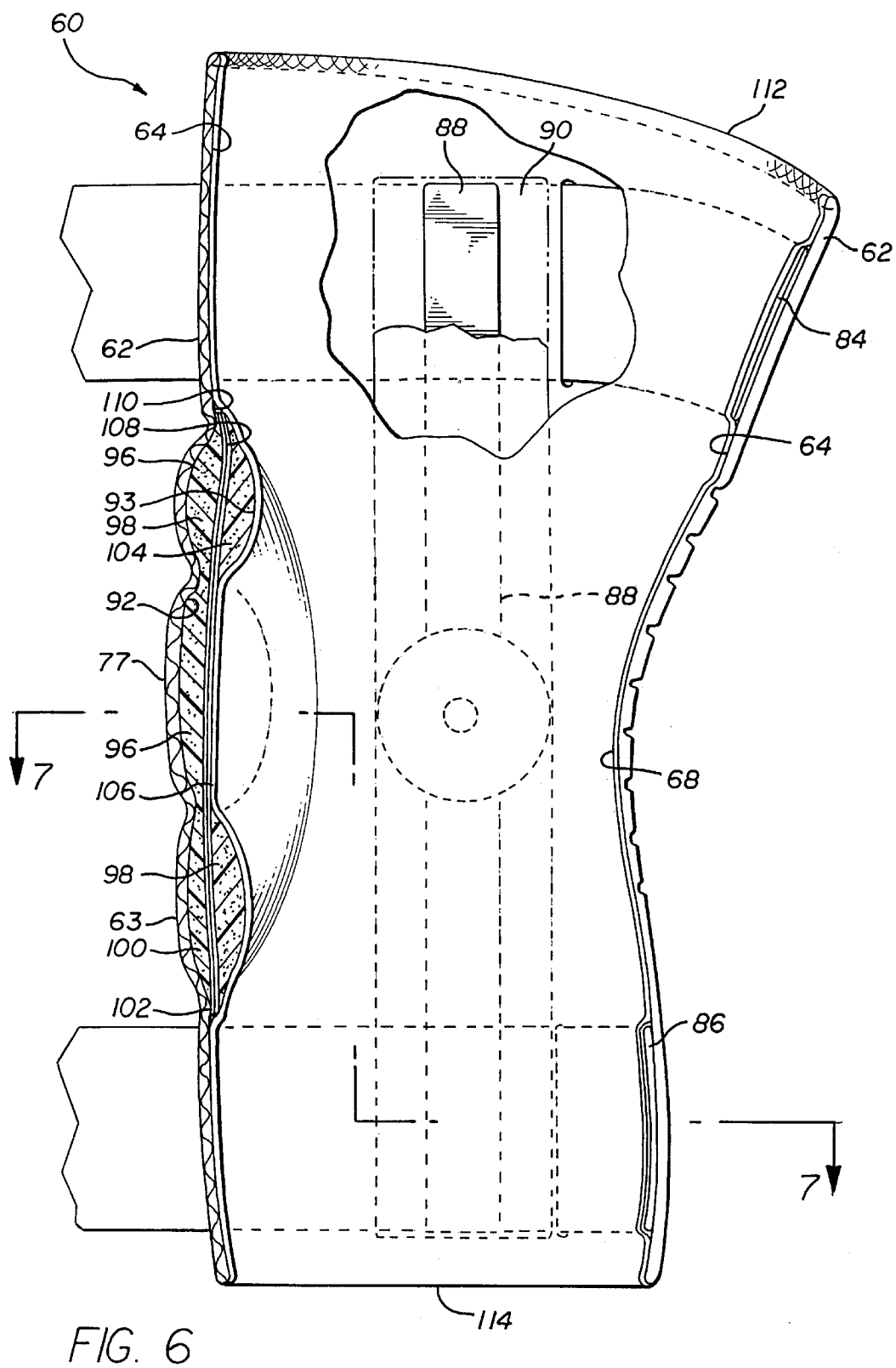
FIG. 6 is a side cross-sectional view of the orthopaedic knee support of FIG. 5 taken in the direction indicated by arrows 6—6 in FIG. 5, with a cut-out to show a portion of a strut-and-hinge assembly attached to the inner surface of the outer resilient layer.

A preferred exemplary embodiment of an orthopaedic knee brace in accordance with the present invention is shown generally at 10 in FIGS. 1–4. Referring initially to FIG. 2, the knee brace includes an outer resilient layer 12 and an inner resilient layer 14.

The outer resilient layer 12 is configured to extend above and below a knee and is comprised of material suitable for surrounding and supporting the knee through compression. A relatively high density closed cell elastomeric material such as a neoprene rubber is generally preferred for outer resilient layer 12 because of its elasticity and the ability to provide support to a body part through compression. Other materials which are stretchable and resilient and have generally comparable properties may be employed.

In those applications where the neoprene rubber (or other material supporting the knee through compression) is vulnerable to damage by way of contact with rough or hard surfaces such as concrete, it is preferable that outer resilient layer 12 further include a thin durable stretchable fabric layer (not shown) which may be laminated to the outer surface 16 of the neoprene layer 12. The provision of such a fabric layer as a protective cover for the material supporting the knee generally increase the durability and life of resilient orthopaedic supports. Such protective outer cover may be formed from of any high strength stretchable fabric, such as brushed nylon. A fabric layer may also be laminated to the inside surface of the neoprene layer to further increase durability and comfort of the orthopaedic support. Lamination may be accomplished using known adhesives or other methods known to those skilled in the art of manufacturing orthopaedic supports.

While the preferred thickness of the outer resilient layer will vary depending upon the body part to be supported, the material or materials selected to provide compression and the nature of the trauma suffered, the outer resilient layer typically will range from about 1/16 of an inch to 3/16 of an inch in thickness.

As best shown in FIG. 1, the outer resilient layer 12 may include an opening 20 in the patellar region 22 of the brace 10 for receiving the knee cap or patella which may be sensitive to pressure. Resilient outer layer 12 is also provided with transverse grooves 24 and corresponding strip pads 26 in the patellar region 22. The strip pads 26 protect the areas above, below and to each side of the knee cap; and they may be of the same thickness as the major areas of the brace. Grooves 24 allow the knee brace to be more easily flexed as is further discussed below.

The transverse grooves 24 and strip pads 26 are preferably formed using a compression molding method disclosed in pending U.S. patent application Ser. No. 08/018,004 cited above. The compression molding method involves the application of heat and pressure to the selected portions of a compression moldable material such as the outer resilient layer 12 so as to form the areas of reduced thickness (and increased density) such as grooves 24. The areas that are not compressed, or which are only slightly compressed, namely, strip pads 26, constitute regions of extra padding. The compressed regions tend to be more stretchable than the uncompressed, or partially compressed, regions. Accordingly, the compression molding method can be used to create areas of varying thickness, density and resiliency along different regions of the outer resilient layer 12.

Referring now to FIGS. 2–4, knee brace 10 also includes an inner resilient layer 14 which is provided between the outer resilient layer 12 and the knee to be supported. The inner resilient layer 14 is coextensive with the outer resilient layer 12 except in the patellar region of the knee where the inner resilient layer 14 does not include a patellar opening.

An inner resilient layer in accordance with the present invention is preferably composed of one or more resilient materials which will provide additional comfort, protection and support for the knee.

As best shown in FIG. 4, the inner resilient layer 14 of FIGS. 1–4 includes a skin-protecting layer 28 adjacent the skin of the knee and an additional layer 30 which is disposed between the skin-protecting layer 28 and the outer resilient layer 12. The skin-protecting layer 28 and the additional layer 30 are preferably laminated together so as to form an integral inner resilient layer.

The skin-protecting layer 28 is preferably composed of a relatively thin non-abrasive non-allergenic porous material which feels comfortable against the user's skin. Suitable materials include such knitted fabrics such as lycra, polyester, nylon, COOLMAX, and polypropylene with lycra being preferred. The porosity of such materials improves the breathability of the support and assists in wicking accumulated perspiration away from the skin underlying the support so as to reduce the likelihood of skin irritation. The additional layer 30 is preferably composed of an relatively low density open cell elastomer such as polyurethane foam. Other suitable materials for additional layer 30 include esters, ethers, ethylenes and polyvinylchloride. The additional layer 30 preferably ranges from about 1/32 to 1/8 of an inch in thickness. If desired, the inner layer 14 may include a third layer 31 as shown in FIG. 4, on the other side of layer 30 from layer 28, which layer 31 would be exposed through the patellar opening. This layer 31 may, for example, be of the same material as layer 28.

In accordance with the present invention, layers 28, 30 and 31 together form an inner resilient layer 14 which, when stretched over the user's knee, only exerts a light restraining force on the patella. This light restraining force assists in maintaining the patella within the patellofemural joint without offsetting the benefits of providing the patellar opening 20 in the outer resilient layer 12.

Notably, the wicking effect of inner resilient layer 14 is enhanced if perspiration can pass through the skin-protecting layer 28 to the additional layer 30. The porosity of layers 28 and 30 and the junction therebetween may be effected by the method by which the two layers are joined together. For example, an adhesive may be used to join the layers together, but most adhesives will render some portion of each layer and the junction between each layers substantially non-porous. By contrast, if layers 28 and 30 are joined using flame lamination methods known in the art, the porosity of each layer and the junction therebetween usually goes substantially undiminished. Accordingly, it is generally preferred to flame laminate layers 28 and 30 together or to join layer 28 and 30 by such other method as does not inhibit the porosity of layers 28 and 30 and the junction therebetween. Where layer 31 is formed from a knitted fabric, it may also be flame laminated to the additional resilient layer 30.

The inner and outer resilient layers are sewn or otherwise secured together so as to form upper and lower rims 32 and 34 of the knee support 10. The inner and outer resilient layers 12 and 14 are not attached along any of their coextensive portions which extend between rims 32 and 34 and thus are freely stretchable and movable relative to one another.

Advantageously, the independence and separateness of the inner and outer resilient layers 12 and 14 render knee brace 10 substantially more comfortable then currently available models. While conventional resilient supports generally cause skin discomfort at points of bending for reasons described above (with or without an integral skin-protecting layer), the separateness of the outer resilient layer 12 of a knee brace enables the outer resilient layer 12 to bunch up at points of bending separate and apart from the inner resilient layer 14 without contacting the skin. While the inner resilient layer 14 will also tend to bunch at points of bending, the stretch characteristics of the inner resilient layer 12 are such that the inner resilient layer does not exert forces against the knee which are likely to be a source of discomfort. These factors, taken together with the non-abrasiveness and porosity of the inner resilient layer 14, render the knee brace 10 substantially more comfortable than currently available supports.

Attention is now directed to certain features of the outer resilient layer 12. Referring to FIGS. 1 and 2, the outer resilient layer 12 includes a pair of spaced apart horizontal slots 36 substantially adjacent the upper rim 32 of the knee brace 10 and a corresponding pair of spaced apart horizontal slots 38 substantially adjacent the lower rim 34 of the brace 10. Slots 36 and 38 are provided to receive adjustable straps 39 and 40, respectively. Adjustable straps 39 and 40 are known in the art.

The straps 39 and 40 provide additional support and prevent the knee brace 10 from slipping during use. Advantageously, the straps 39 and 40 extend through the slots 36 and 38 and around the back of the knee between the inner and outer layers 12 and 14 thereby concealing a substantial portion of each strap and reducing the likelihood that the straps will catch on external objects when the brace is worn. Advantageously, slots 36 and 38 act to guide and limit the movement of straps 39 and 40 so that there may be no need to sew the free running straps to the brace itself.

As can be seen from FIGS. 1, 2, and 4, a pair of substantial adjacent lateral stays 42 may be provided between inner and outer resilient layers 12 and 14 to provide lateral support for knee. The stays are fixed in place between a retaining member 44 and the inner surface 18 of the outer resilient layer 12. Retaining member 44 is preferably comprised of a resilient material which is not likely to be torn or punctured by the stays and which will provide protective padding for the user. Suitable materials include a relatively high density elastomer such as neoprene rubber. Resilient member 44 may be secured to outer resilient layer 12 with stitches or an adhesive or a combination of the two.

As best seen in FIGS. 2 and 3, the knee brace 10 also includes an horseshoe-shaped patellar buttress 46 which is attached to the inner surface 47 of the inner resilient layer 14 using conventional means. The patellar buttress 46 surrounds and protects the upper and side portions of the patella. Patellar buttress 46 is also serves to maintain the patella properly within the patellofemural joint. Preferably, buttress 46 is formed from a relatively low density open cell elastomeric member 48 such as polyurethane foam, esters, ethers, ethylenes, polypropylenes and polyvinylchloride with polyurethane foam being preferred. Buttress 46 may also include a thin durable fabric layer 50 which is preferably laminated to the elastomeric member prior to attachment of the buttress 46 to the inner resilient layer. Durable fabric layer 50 may be composed of any of the knitted fabrics identified hereinabove.

Now referring to FIGS. 5–7, a second preferred embodiment of a knee brace in accordance with the present invention is shown generally at 60. Knee brace 60, like knee brace 10, includes two substantially independently movable and stretchable layers, outer resilient layer 62 and inner resilient layer 64. However, outer resilient layer 62 does not include a patellar opening.

The outer and inner resilient layers 62 and 64 are substantially similar in composition to the outer and inner resilient layers of knee brace 10. As with knee brace 10, outer resilient layer 62 preferably includes a neoprene rubber layer 63 with a protective fabric cover (not shown) laminated thereto, and inner resilient layer 64 preferably includes a relatively thin non-abrasive porous fabric layer (not shown) adjacent the knee and a relatively low density elastomeric layer 68 disposed between the fabric layer and outer resilient layer 62.

As best shown in FIG. 5, the outer resilient layer 62 includes substantially annular grooves 70 and 72 and corresponding protective pads 74 and 76 in the patellar region 78. Protective pad 74 covers and protects the patella. Protective pad 76 protects the areas above, below and to each side of the patella. Protective pads 74 and 76 protrude outwardly from the outer surface 77 of the outer resilient layer 62. The preferred method for forming grooves 70 and 72 and protective pads 74 and 76 is discussed hereinbelow.

As will be noted from FIGS. 5–7, knee brace 60 includes a variety of supplemental orthopaedic members between inner and outer resilient layers 62 and 64. Referring first to FIGS. 5 and 7, the outer resilient layer 62 includes two pairs of horizontal slots 80 and 82 for receiving adjustable straps 84 and 86, respectively. As with the embodiment illustrated in FIGS. 1–4, the straps 84 and 86 extend through the slots and around the back of the knee between the inner and outer resilient layers. Each strap 84 and 86 is sewn to the outer resilient layer 62 adjacent one of the two slots through which each strap extends as is best shown at 87 in FIG. 7. Notably, the attached portion of each strap 84 and 86 extends substantially perpendicular to the length of the straps and thus does not unduly inhibit the adjustability of the straps.

Knee brace 60 is also provided with strut-and-hinge assemblies 88 between inner and outer resilient layers 62 and 64, each assembly 88 providing lateral support for the knee. Each assembly 88 is fixed in place between a retaining member 90 and the inner surface 92 of the outer resilient layer 62. As discussed above, retaining member 90 is preferably comprised of a resilient material which is not likely to be torn or punctured and which will provide protective padding for the user. Each assembly 88 may be secured to the inner surface 92 of outer resilient layer 62 using the compression molding method discussed hereinafter.

Attention will now be directed to supplemental orthopaedic padded members 96 and 98. Padded member 96 increases the thickness of the brace in the area corresponding with pads 74 and 76. Padded member 98 increases the thickness of the brace in the area corresponding to pad 76. Padded member 98 also helps to locate the patella within the patellofemural joint. Padded member 96 is secured to the inner surface 92 of the outer resilient layer 62. Padded member 98 is secured to the outer surface 93 of the inner resilient layer 64. Padded member 96 includes a resilient member 100 and a thin fabric layer 102. Padded member 98 includes a resilient member 104 and a thin fabric layer 106.

The resilient members 100 and 104 are preferably composed of a relatively low density elastomer such as polyurethane foam but may also be composed of a relatively high density elastomer such as neoprene rubber or any other material suitable for the desired orthopaedic function. The fabric layers 102 and 106 may be composed of any of the fabrics describe hereinabove.

Padded members 96 and 98 are each cut from a sheet of stock of a preferred resilient material which has been laminated with a preferred fabric layer. Resilient layer 100 and fabric layer 104 of padded member 96 are completely overlapping. By contrast, the resilient layer 102 and fabric layer 106 of padded member 98 only overlap perimetrally as resilient member 102 includes a centrally located patellar opening 108 wherein resilient material has been removed.

Resilient member 102 is preferably fixed to the inner surface 92 of the outer resilient layer 62 using a suitable pressure sensitive adhesive or an adhesive such as 3M Adhesive No. 48NF. Thereafter, outer resilient layer 62 and resilient member 102 are together subjected to varying amounts of heat and pressure using the compression molding technique described in pending U.S. patent application Ser. No. 08/018,004 in the name of Grim et al. The heat and pressure are used to reduce the thickness (and increase the density) of various portions of both the outer resilient layer 62 and the resilient member 102 as best shown in FIGS. 5–7.

Advantageously, the compression molding apparatus is configured to exert pressure against the outer resilient layer 62 so as to form compressed areas corresponding with grooves 70 and 72 and to exert pressure against the portions of the padded member 96 corresponding with protective pads 74 and 76 such that padded member 96 creates a depression in inner surface 92 of the outer resilient layer 62 and causes the outer surface 77 of the outer resilient layer to bulge outwardly to form outwardly projecting orthopaedic pads (consisting of protective pads 72 and 74 and the corresponding portions of the underlying padded member 96).

While the outwardly projecting pads of knee brace 60 provide the patellar region of the underlying knee with protection in manner which might be deemed comparable to the protection afforded to such region by additional padding attached to the outer surface of a conventional resilient brace, it will be appreciated by those skilled in the art that the outwardly projecting pads of knee brace 60 are not secured to such outer surface and thus cannot be torn away from outer resilient layer 62 upon contact with external objects. Accordingly, a more durable knee brace is provided.

Those skilled in the art will also note that, in using the above-described compression molding method to increase the thickness of knee brace 60, a padded member 96 may include a non-adjoining surface 108 which is substantially flush with the portion 110 of the inner surface 92 adjacent the padded member 96 as best shown in FIGS. 6–7. The non-adjoining surface 108 does not project outwardly from inner surface 92 towards the knee in any substantial manner and thus does not increase pressure on the patella and surrounding tissue as would such a protective pad secured to the inner surface of a resilient orthopaedic support using conventional means.

It will also be understood that resilient member 100 and the outer resilient layer 62 may be joined without the use of adhesive if resilient member 100 and outer resilient layer 62 are composed of a compatible materials which may be heat laminated together during the compression molding process.

The above described compression molding method is also used in securing padded member 98 to the outer surface 93 of the inner resilient layer 64. For this application, the compression molding apparatus is configured to exert pressure against the outer resilient layer 62 such that the padded member 98 creates a depression in the outer surface 93 of the inner resilient layer 64 and causes the inner surface of the inner resilient layer to bulge outwardly towards the underlying knee as best seen in FIGS. 6 and 7.

While resilient members 100 and 104 are preferably composed of a relatively low density polyurethane foam, these resilient members may be composed of any suitable material including without limitation neoprene rubber. The preferred material and its preferred thickness, density and resiliency (before and after compression molding) will vary depending upon many factors including the body part to be supported and the orthopaedic function to be performed by each padded member. Resilient members 100 and 104 may also be pre-inflated bladders with a resilient material such as polyurethane foam enclosed therein.

Preferably, the foregoing described compression molding method is used to attach the strut-and-hinge assemblies 88 (and other supplemental orthopaedic members) to the inner surface 92 of the outer resilient layer 62 (or the outer surface 93 of the inner resilient layer 64, if desired). For this application, the compression molding apparatus may be configured to exert pressure against the outer surface 77 of the outer resilient layer 62 so as to form a compressed area (corresponding to groove 97 of FIG. 5) which circumscribes each underlying assembly 88. The preferred apparatus is also configured to simultaneously exert pressure against retaining member 90 such that retaining member 90 and assembly 88 together create a depression in the inner surface 92 of the outer resilient layer 62 and cause the outer surface 77 of the outer resilient layer to bulge outwardly. Advantageously, retaining member 90 forms a substantially flush interface with the portion of the inner surface 92 adjacent the retaining member 90. Accordingly, assembly 88 is comfortable and non-binding despite being located between outer resilient layer 62 and the underlying knee.

Those skilled in the art will also appreciate that the foregoing disclosed compression molding method allows a manufacturer to increase the thickness of an orthopaedic support formed from a sheet of resilient material and that the manufacturer may therefore be able to meet desired specifications using a thinner sheet of stock in conjunction with additional resilient members. This may result in considerable cost savings to manufacturer and thus constitutes a significant improvement over the invention disclosed in pending U.S. patent application Ser. No. 08/018,004.

It should be noted that resilient orthopaedic braces formed in accordance with the present invention are typically subjected to temperatures ranging from ambient temperatures to 315° F. during the compression molding process, with temperatures ranging from 310° F. to 315° F. being preferred.

Those skilled in the art will understand that preferred adhesive for joining supplemental orthopaedic members to the inner or outer resilient layer may be selected from the group of adhesives which do not lose their adhesive characteristic when subjected to high temperatures and which are otherwise compatible with the compression molding process. Any other adhesives used in accordance with the present invention may also be compatible with the compression molding process.

After the preferred supplemental orthopaedic members have been attached to the outer or inner resilient layers 62 and 64, assembly of brace 60 can be completed by joining the outer and inner resilient layers 62 and 64 together to form lower and upper rims 112 and 114. As with the first preferred embodiment shown in FIGS. 1–4, the outer and inner resilient layers are both separable and independently stretchable along the entire portions of each extending between the upper and lower rims.

The inner and outer layers may be adjoined by stitches, by using a suitable adhesive, alone or in conjunction with stitches, by heat bonding, provided the portions of the inner and outer layers to be adjoined are composed of compatible materials as discussed above, or by any other suitable method.

Regarding the final assembly of knee brace 60, it is noted that outer resilient layer 62 includes a longitudinal seam 116 which extends from the lower rim 114 through the popliteal area of the knee up to the upper rim 112. Seams located in the popliteal area of the knee in resilient orthopaedic braces are a common source of discomfort to the user. The discomfort associated with such seams is mitigated by the provision of inner resilient layer 64 constructed without seams adjacent the popliteal area of the knee as is best shown in FIG. 7. As can be seen therein, the seams 118 in the inner resilient layer extend between the lower and upper rims 112 and 114 along lateral portions of the knee brace 60.

Referring now to FIG. 8, an elbow brace in accordance with the present invention is shown generally at 120. The elbow brace includes an outer resilient layer 122 having an opening 124 to relieve pressure which would otherwise be exerted at the back of the elbow. The elbow brace also includes an inner resilient layer 126 which is substantially coextensive with the outer resilient layer. As with the knee braces of FIGS. 1–4 and 5–7, the inner and outer resilient layers of elbow brace 120 are only adjoined at the upper and lower rims 128 and 130 with the portions of each layer extending therebetween being independently moveable and stretchable.

Having thus described exemplary preferred embodiments of the present invention, it will be apparent to those skilled in the art that the within disclosures are exemplary only and that various other alternatives, adaptations and modifications may be accomplished which still fall within the scope and spirit of the present invention. In particular, it will be appreciated by those skilled in the art that an inner resilient layer in accordance with the present invention need only be generally coextensive with a substantial portion of the outer resilient layer and thus need not completely surround the portion of human body to be supported and need not extend fully between the upper and lower rims of the outer resilient layer. It will also be appreciated by those skilled in the art that the inner and outer resilient layers may be joined at other locations other than or in addition to the upper and lower rims of the outer resilient layer and still fall within the scope and spirit of the present invention so long as the greater part of the coextensive portions of each layer are independently moveable and stretchable. Concerning the relative magnitude of the force applied by the inner and outer layers, in one preferred embodiment, the force provided by the inner layer, for example, on the patella, is one-half or less than that which would be provided if the outer layer also extended over the patella.

Those skilled in the art will also understand that a resilient orthopaedic support in accordance with the present invention may provide non-uniform compression to a supported body part without having two generally coextensive resilient layers. Rather, the orthopaedic support may include first resilient member composed of a material such as neoprene rubber configured to support a portion of the human anatomy through compression and having an aperture configured to relieve the pressure exerted by the first resilient member from a discrete area of the supported body member. Such an orthopaedic brace would also include a second resilient member in the shape of the aperture of the first resilient member and composed of a material suitable for exerting a light restraining force on the discrete area of the supported body part. The second resilient member is sewn or otherwise attached to the inside or outside surface of the first resilient member so as to extend across the aperture in the first resilient member. Preferably, the second resilient member would be comprised of a relatively light density polyurethane foam, each side of which would be laminated with a thin fabric layer of the type described hereinabove.

Those skilled in the art will also appreciate that a wide variety of compression moldable supplemental orthopaedic members may be adjoined to a selected area of a resilient member or layer and thereafter subjected to heat and compression so as to form orthopaedic supports having the characteristics described hereinabove.

Accordingly, the scope of the present invention is not limited to the specific embodiments as illustrated herein, but is limited only by the following claims and equivalents thereof.

What is claimed is:

1. A knee brace comprising:
   an outer resilient layer configured to extend above and below a knee joint, said outer resilient layer being comprised of a material suitable for surrounding and supporting a knee through compression and having a patellar opening for receiving the patella of the knee; and
   an inner resilient layer generally coextensive with at least a substantial portion of said outer resilient layer and extending across said patellar opening to exert a relatively light restraining force on the patella;
   said inner and outer resilient layers being secured together.

2. A knee brace according to claim 1 wherein said inner and outer resilient layers are secured together in discrete zones but are otherwise freely stretchable or movable relative to one another.

3. A knee brace according to claim 1 wherein said inner resilient layer extends around the knee to be supported.

4. A knee brace according to claim 1 wherein said inner resilient layer further comprises a skin-protecting layer comprised of non-abrasive porous material.

5. A knee brace according to claim 1 wherein said inner resilient layer is comprised of a non-abrasive porous fabric layer adjacent the knee and a relatively low density foam layer disposed between said fabric layer and said outer resilient layer.

6. A knee brace according to claim 1 further comprising a supplemental orthopaedic member mounted at least in part between said inner and outer resilient layers.

7. A knee brace according to claim 6 wherein said supplemental orthopaedic member comprises at least one substantially free running strap.

8. A knee brace according to claim 6 wherein said supplemental orthopaedic member comprises lateral support means.

9. A knee brace according to claim 6 wherein said supplemental orthopaedic member comprises an orthopaedic pad.

10. A knee brace according to claim 6 wherein said supplemental orthopaedic member comprises a bladder.

11. A knee brace according to claim 1 wherein said inner resilient layer is seamless adjacent the popliteal area of the knee.

12. An orthopaedic support for a knee comprising:
an outer resilient layer configured to extend above and below a knee joint, said outer resilient layer being comprised of a material suitable for surrounding and supporting a knee through compression and having a patellar opening for receiving the patella of the knee; and
an inner resilient layer configured to extend across said patellar opening to exert a relatively light restraining force on the patella;
said outer resilient layer being a higher density stretch material, said inner resilient layer being a lower density stretch material;
wherein said inner resilient layer is adapted to be disposed in between said outer resilient layer and the knee when said orthopaedic support is positioned on the knee during use, and wherein at least a substantial portion of the inner resilient layer is independently movable and stretchable relative to said outer layer.

13. An orthopaedic support for a portion of the human anatomy comprising:
a first resilient member configured to extend around a portion of the human anatomy, said first resilient member being comprised of a material suitable for surrounding and supporting said portion of the human anatomy through compression, said first resilient member having an aperture configured to relieve pressure exerted by said first resilient member from a discrete area of the supported portion of the human anatomy; and
a second resilient member configured to extend across said aperture to exert a relatively light restraining force on said discrete area, said second resilient member being generally coextensive with a substantial portion of said first resilient member.

14. An orthopaedic support comprising:
a stretchable outer resilient layer comprising foam sheet material configured to extend around a portion of the human anatomy, said outer resilient layer being comprised of a material suitable for surrounding and supporting the portion of the human anatomy through compression; and
a stretchable inner resilient layer comprising foam sheet material that is generally coextensive with at least a substantial portion of said outer resilient layer, the greater part of the coextensive portions of said inner and outer resilient layers being independently movable or stretchable;
said orthopaedic support further comprising a supplemental resilient member adjacent a selected area of said outer or inner resilient layer, said supplemental resilient member and said selected area of said adjacent resilient layer being comprised of compression moldable materials which together have been subjected to heat and compression so as to alter the thickness and density of a discrete portion of said supplemental resilient member and said selected area of said adjacent resilient layer.

15. An orthopaedic support according to claim 14 wherein said outer resilient layer has an inner surface which is disposed towards said portion of the human anatomy and an outer surface which is disposed away from the portion of the human anatomy and wherein said supplemental resilient member adjoins said inner surface.

16. An orthopaedic support according to claim 15 wherein said supplemental resilient member has a non-adjoining surface disposed towards the portion of the human anatomy and an adjoining surface adjacent said inner surface of said outer resilient layer and wherein said non-adjoining surface is substantially flush with a portion of said inner surface of said outer resilient layer adjacent said selected area.

17. An orthopaedic support according to claim 15 wherein said supplemental resilient member and said selected portion of said outer resilient layer form an outwardly projecting padded member.

18. An orthopaedic support according to claim 14 wherein said inner resilient layer has an inner surface which is disposed towards the portion of the human anatomy and an outer surface which is disposed away from the portion of the human anatomy and wherein said supplemental resilient member adjoins said outer surface.

19. An orthopaedic support according to claim 18 wherein said supplemental resilient member has a non-adjoining surface disposed away from said portion of the human anatomy and an adjoining surface adjacent said outer surface of said inner resilient layer and wherein said non-adjoining surface is substantially flush with a portion of said outer surface of said inner resilient layer adjacent said selected area.

20. An orthopaedic support according to claim 18 wherein said supplemental resilient member and said selected portion of said inner resilient layer form an inwardly projecting padded member.

21. An orthopaedic support according to claim 14 wherein said outer resilient layer or said supplemental resilient member is comprised of a relatively high density closed cell material.

22. An orthopaedic support according to claim 14 wherein said supplemental resilient member or said inner resilient layer is comprised of a relatively low density open cell material.

23. An orthopaedic support for surrounding and supporting a portion of the human anatomy through compression comprising:
a first resilient member having first and second opposing surfaces, said first resilient member having a substantial extent and including at least one restricted area where the human anatomy is subject to stress or impact; and
a second resilient member adjacent said restricted area of said first resilient member, said second resilient member and said restricted area of said first resilient member being comprised of compression moldable materials which together have been subjected to heat and compression so as to alter the thickness and density of a discrete portion of said second resilient member and said restricted area of said first resilient member.

24. An orthopaedic support according to claim 23 wherein said second resilient member has a first surface disposed away from said first resilient member and second surface disposed towards said first resilient member and wherein said first surface is substantially flush with a portion of said first resilient member which is adjacent said restricted area.

25. An orthopaedic support according to claim 23 wherein said first resilient member has a first surface which adjoins said second resilient member and a second surface disposed away from said second resilient member and wherein said first and second resilient members form a padded member which projects outwardly from said second surface of said first resilient member.

26. An orthopaedic support for a knee comprising:

an outer resilient layer configured to extend above and below a knee joint, said outer resilient layer being comprised of a material suitable for surrounding and supporting a knee through compression and having a patellar opening for receiving the patella of the knee; and an inner resilient layer configured to extend across said patellar opening to exert a relatively light restraining force on the patella;

wherein, when the orthopaedic support is mounted about a knee, said inner resilient layer is disposed in between said outer resilient layer and the knee and wherein said inner resilient layer is stretchable and movable independently of said outer layer at said patellar opening.

27. An orthopaedic support comprising:

an outer resilient layer configured to extend around a portion of the human anatomy, said outer resilient layer being comprised of a material suitable for surrounding and supporting the portion of the human anatomy through compression; and an inner resilient layer generally coextensive with at least a substantial portion of said outer resilient layer, the greater part of the coextensive portions of said inner and outer resilient layers being independently movable or stretchable;

wherein at least one region of the orthopaedic support has been compression molded to improve the function of the support.

* * * * *